(12) United States Patent
Adler et al.

(10) Patent No.: US 6,248,062 B1
(45) Date of Patent: Jun. 19, 2001

(54) LAPAROSCOPIC RETRACTOR

(75) Inventors: Jonathan Adler, Upper Brookville; Bernd Ascher, Islip Terrace; Leonard Coraci, Jr., Selden, all of NY (US)

(73) Assignee: Flexbar Machine Corp., Islandia, NY (US)

( * ) Notice: Subject to any disclaimer, the term of this patent is extended or adjusted under 35 U.S.C. 154(b) by 0 days.

(21) Appl. No.: 09/710,301

(22) Filed: Nov. 9, 2000

(51) Int. Cl.$^7$ ........................................... A61B 1/32
(52) U.S. Cl. ............................................... 600/204
(58) Field of Search ..................... 600/204, 210, 600/216, 215, 141, 142, 146, 147

(56) References Cited

U.S. PATENT DOCUMENTS

| | | | |
|---|---|---|---|
| 2,510,198 | * 6/1950 | Tesmer | 248/229.25 |
| 4,239,036 | * 12/1980 | Krieger | 600/216 |
| 4,688,554 | * 8/1987 | Habib | 600/146 |
| 5,448,989 | * 9/1995 | Heckele | 600/142 |
| 5,522,788 | * 6/1996 | Kuzmak | 600/141 |

* cited by examiner

Primary Examiner—Gene Mancene
Assistant Examiner—Eduardo C. Robert
(74) Attorney, Agent, or Firm—Collard & Roe, P.C.

(57) ABSTRACT

A laparoscopic retractor comprises a shaft having a distal end, a proximal end and a channel extending longitudinally from the distal end to the proximal end, and a handle connected to the proximal end of the shaft and having a longitudinal channel therethrough. There are a plurality of links pivotally connected in a linear arrangement, with one of the links connected to the distal end of the shaft. Each link has a longitudinal channel therethrough. The shaft and links form a continuous line terminating in a tip formed by an end link. There is a cable extending from the tip through the channels in the links, shaft and handle and an adjustment mechanism connected to the handle opposite the shaft and connected to the cable. There is spring mounted between the handle and adjustment mechanism to bias movement of the adjustment mechanism relative to the handle. The adjustment mechanism can be locked in a biased position wherein the cable is extended and the links rest in a straight line for insertion through a cannula, and can be released so that the cable is retracted an pulls the links into a curved arrangement for use during surgery. There is also a flush port for internal cleaning.

13 Claims, 2 Drawing Sheets

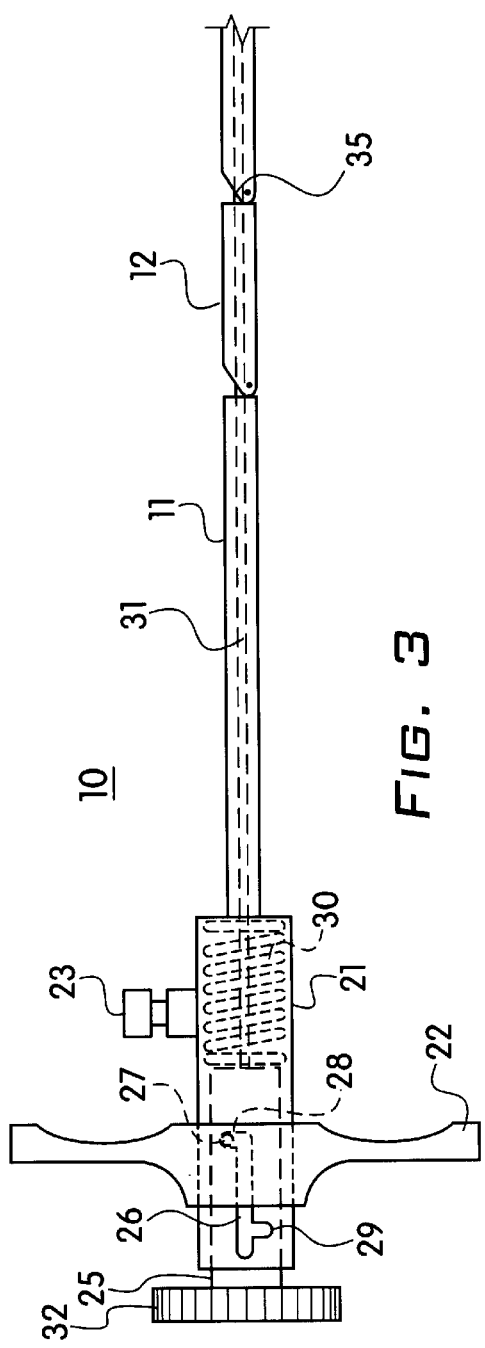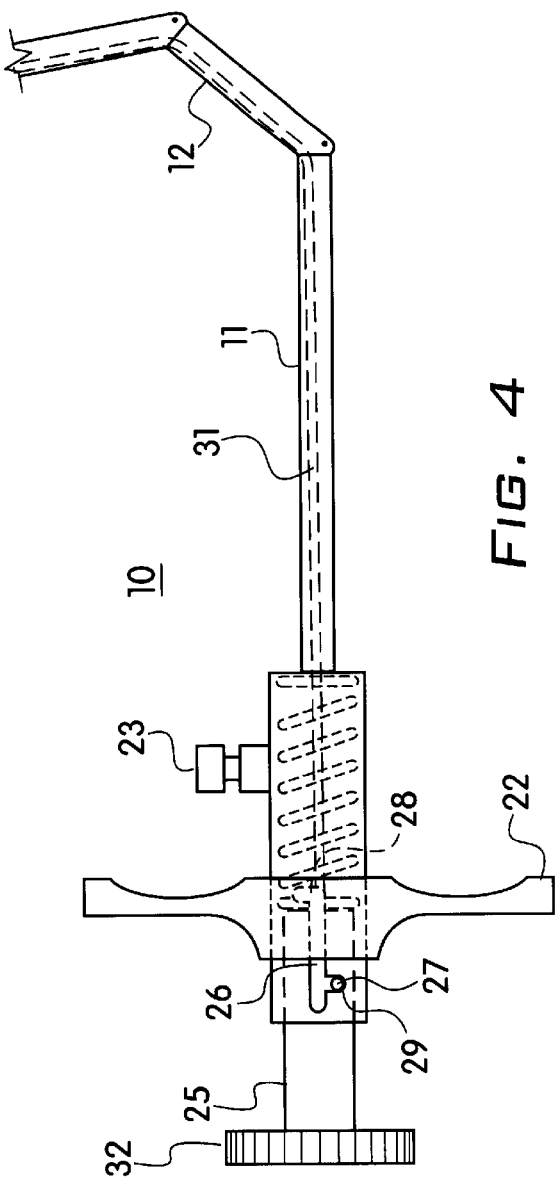

LAPAROSCOPIC RETRACTOR

BACKGROUND OF THE INVENTION

1. Field of the Invention

This invention relates to a retractor for use in laparoscopic surgery. In particular, the invention relates to a retractor that can be easily moved from a locked, straight position for insertion through a cannula, to an unlocked, self-forming curved or rounded position after the retractor is within the body.

2. The Prior Art

In laparoscopic surgery, the surgery is performed by making a small incision in the body and placing a cannula through the incision to the area to be operated on. The surgical instruments are then inserted through the cannula an manipulated from outside the body. Consequently, all of the instruments used in laparoscopic surgery must be small enough to fit through the cannula. It is often necessary during the surgery to move tissues or organs out of the way with a retractor. With large organs such as the liver, a retractor with a large surface area is needed. However, given the small diameter of the cannula, it is difficult to insert a suitable retractor into the surgical site.

There have been many attempts to devise a retractor that is suitable for laparoscopic or arthroscopic use. For example, U.S. Pat. No. 5,685,826 to Bonutti discloses a retractor having a mechanically expandible end portion. After the retractor is inserted into the surgical area, the tip of the retractor is pulled back, causing the side walls to fold outward, forming a plurality of radial arms.

Another retractor is produced by Genzyme Surgical Products. This retractor comprises a series of links held together by multiple cables. When the cables are tightened, the links form a predetermined shape. When the cables are loose, the links lie straight and can be fed through a cannula. The links are tightened by turning a screw until the desired shape is achieved.

While this device is an improvement over previous retractors, it is difficult to turn the screw and adjust the retractor during surgery.

SUMMARY OF THE INVENTION

It is therefore an object of the present invention to provide a laparoscopic retractor that is capable of moving large organs out of the way during surgery, yet small enough to fit through a cannula.

It is another object of the invention to provide a laparoscopic retractor that can be easily adjusted from the straight to the curved position during surgery.

It is another object of the invention to provide a laparoscopic retractor that is simple to manufacture and use.

These and other objects of the invention are accomplished by a laparoscopic retractor comprising a shaft having a distal end, a proximal end and a channel extending longitudinally from the distal end to the proximal end, and a handle connected to the proximal end of the shaft and having a longitudinal channel therethrough. There are a plurality of links pivotally connected in a linear arrangement, with one of the links connected to the distal end of the shaft. Each link has a longitudinal channel therethrough. The shaft and links form a continuous line terminating in a tip formed by an end link. There is a cable extending from the tip through the channels in the links, shaft and handle and an adjustment mechanism connected to the handle opposite the shaft and connected to the cable. There is spring mounted between the handle and adjustment mechanism to bias movement of the adjustment mechanism relative to the handle. The adjustment mechanism can be locked in a biased position wherein the cable is extended and the links rest in a straight line for insertion through a cannula, and can be released so that the cable is retracted an pulls the links into a curved arrangement for use during surgery.

The means for biasing the locking mechanism comprises a protrusion on the locking mechanism, and a channel within the handle having an L-shaped end. Pressing the locking mechanism toward the handle causes the protrusion (or lock pin) to slide down the channel and causes cable to extend, and twisting the locking mechanism forces the protrusion (or lock pin) into a the perpendicular L portion and locks the retractor into an extended position. To secure the retractor into the curved position there is a perpendicular cutout in the channel near the top, so that twisting the protrusion (or lock pin) into the cutout secures the cable in a retracted position, maintaining the links into a curved or rounded arrangement.

The locking mechanism comprises a shaft extending into the channel of the handle at one end and having a knob at the other end. The handle comprises at least two arms extending perpendicular to the longitudinal channel, for holding the retractor during surgery. The shaft, links, handle and adjustment mechanism are preferably made of stainless steel.

There are at least three links, so that the retractor can form a suitably curved arrangement for retracting organs during surgery. Preferably, there are five or more links, thus allowing for a complete circular curvature to be formed.

The tip on the end link is rounded and closed to facilitate sliding the retractor into a cannula.

In the curved arrangement, the links preferably form a closed loop so that the retractor can easily lift large organs and other structures out of the way during surgery. The loop has a diameter of about 2 to 3 inches.

The links are connected to each other via hinges. Preferably, each hinge is comprised of a pin inserted (pressed fit) through holes in the ends of adjacent links.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 3 shows a side cross-sectional view of the handle portion of the retractor in the straight position; and FIG. 4 shows a side-cross-sectional view of the retractor in the curved position.

DETAILED DESCRIPTION OF THE PREFERRED EMBODIMENT

Figure 1:
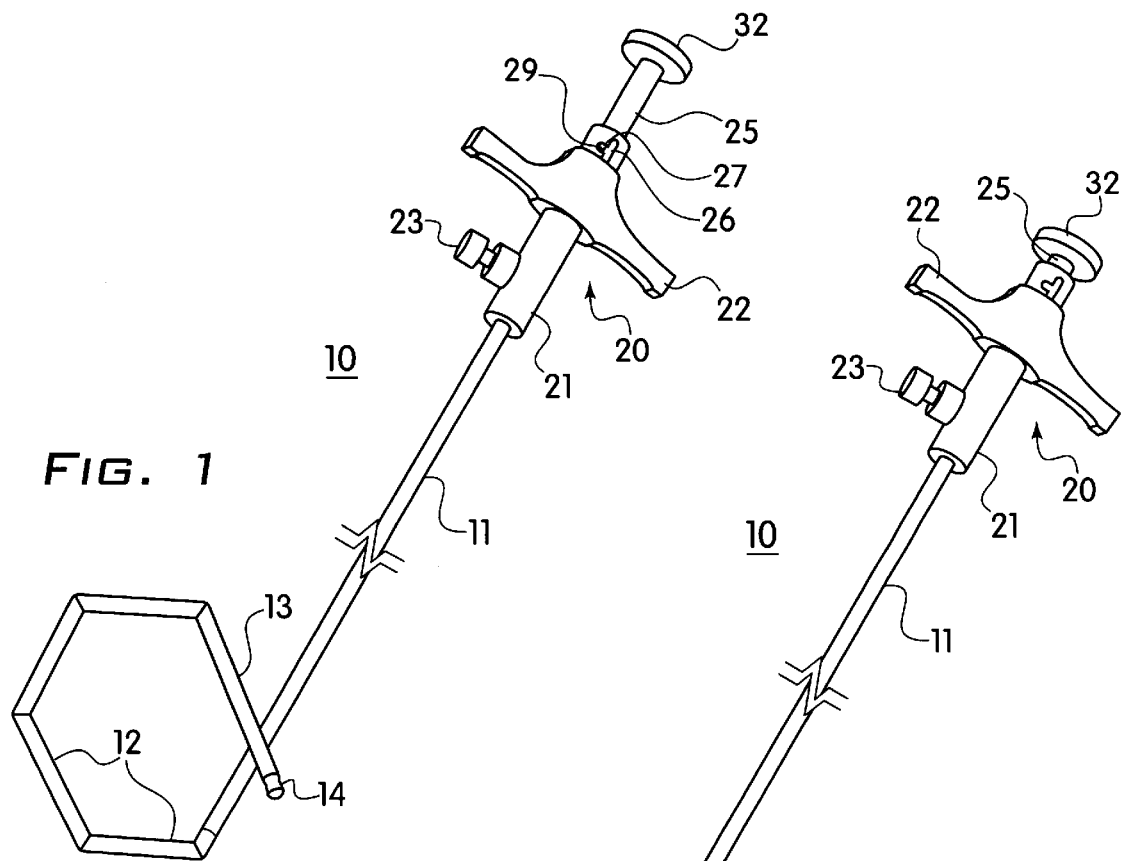
FIG. 1 shows a side perspective view of the retractor in a curved position.
Figure 2:
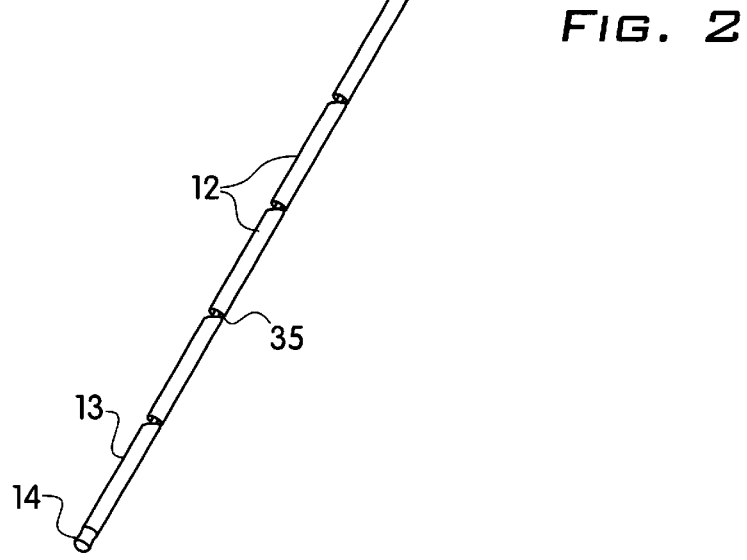
FIG. 2 shows a side perspective view of the retractor in a straight position.

Referring now in detail to the drawings and, in particular, FIGS. 1 and 2 show the retractor 10 according to the invention. Retractor 10 comprises a handle portion 20 connected to a hollow shaft 11. Shaft 11 is pivotally connected at its distal end to a series of links 12, terminating in an end link 13, having a closed rounded end. Shaft 11 and links 12, 13 are connected to each other via hinges 35. Hinges 35 are formed by a pin inserted (pressed fit) into holes in adjacent links 12, 13.

Handle portion 20 comprises a cylinder 21 integrally formed with perpendicular arms 22 to allow a surgeon to easily hold the retractor during use. Cylinder 21 is hollow and is fixedly connected to shaft 11. A Luer-Loc flush port and cap 23 is located on cylinder 21 for internal cleaning. The cap is removed for cleaning using standard hospital flush systems.

As shown in FIGS. 3 and 4, a cable 31 runs through cylinder 21, shaft 11 and links 12 and 13. The end of cable 31 is connected to a shaft 25 that is slidably inserted within cylinder 21. Shaft 25 terminates in a knob 32. A spring 30 is mounted within cylinder 21 to pull cable 30 and cause links 12, 13 to bend into a closed loop, as shown in FIG. 1. Preferably, the closed loop is approximately 2–3 inches in diameter. Retractors of other dimensions could also be made.

There is a slot 26 within cylinder 21 that allows retractor 10 to be locked in either the straight or curved position. Slot 26 has an L-shaped bottom portion 28, and an additional perpendicular slot 29. Shaft 25 has a protrusion that extends through slot 26. To lock retractor 10 into a straight position so that it can be threaded through a cannula, knob 32 is pressed, causing shaft 25 to extend into cylinder 21. This causes cable 30 to extend and allow links 12, 13 to straighten. Once a straight position is achieved, knob 32 is twisted, causing protrusion 27 to slide into bottom portion L-shaped portion 28. This locks retractor 10 into a straight position. To unlock retractor 10, knob 32 is twisted in the opposite direction, causing protrusion 27 to slide up slot 26 and pull cable 31. This causes links 12, 13 to curl into the curved position. Retractor 10 can then be locked into the curved position by twisting knob 32 until protrusion 27 slides within perpendicular slot 29. To unlock retractor 10, knob 32 is then twisted in the opposite direction.

Accordingly, while only one embodiment of the present invention has been shown and described, it is obvious that many changes and modifications may be made thereunto without departing from the spirit and scope of the invention.

What is claimed is:

1. A laparoscopic retractor, comprising:
   a shaft having a distal end, a proximal end and a channel extending longitudinally from the distal end to the proximal end;
   a handle connected to the proximal end of the shaft and having a longitudinal channel therethrough;
   a plurality of links pivotally connected in a linear arrangement, with one of said links connected to the distal end of the shaft and each link having a longitudinal channel therethrough, wherein said shaft and said links form a continuous line terminating in a tip formed by an end link;
   a cable extending from the tip through the channels in the links, shaft and handle;
   an adjustment mechanism connected to the handle opposite the shaft, said adjustment mechanism connected to the cable;
   a spring mounted to the handle and adjustment mechanism to bias movement of the adjustment mechanism relative to the handle; and
   means for locking the adjustment mechanism in a biased position wherein the cable is extended and the links rest in a straight line, and for releasing the adjustment mechanism wherein the cable is retracted and pulls the links into a curved arrangement.

2. The retractor according to claim 1, wherein the means for biasing the locking mechanism comprises a protrusion on the locking mechanism, and a channel within the handle, said channel having an L-shaped end, such that pressing the locking mechanism toward the handle causes the protrusion to slide down the channel and causes cable to extend, placing the retractor into a straight position, and twisting the locking mechanism forces the protrusion into the L-shaped end and locks the retractor into the straight position.

3. The retractor according to claim 2, further comprising a perpendicular cutout on the channel, wherein twisting the protrusion into the cutout locks the cable in a retracted position, forcing the links into the curved arrangement.

4. The retractor according to claim 2, wherein the locking mechanism comprises a shaft extending into the channel of the handle at one end and having a knob at the other end.

5. The retractor according to claim 1, wherein the handle comprises at least two arms extending perpendicular to the longitudinal channel, for holding the retractor during surgery.

6. The retractor according to claim 1, wherein the shaft, links, handle and adjustment mechanism are made of steel.

7. The retractor according to claim 1, wherein there are at least three links.

8. The retractor according to claim 1, wherein there are five links.

9. The retractor according to claim 1, wherein the tip on the end link is rounded and closed.

10. The retractor according to claim 1, wherein in the curved arrangement, the links form a closed loop.

11. The retractor according to claim 10, wherein the loop has a diameter of about 2 to 3 inches.

12. The retractor according to claim 1, wherein the links are connected to each other via hinges.

13. The retractor according to claim 12, wherein each hinge is comprised of a pin press fit through holes in adjacent links.

* * * * *